United States Patent
Tanouchi et al.

(10) Patent No.: US 6,346,276 B1
(45) Date of Patent: Feb. 12, 2002

(54) COMPOSITION CONTAINING USEFUL SUBSTANCES ORIGINATING IN FISHES AND SHELLFISHES AND PROCESS FOR THE PREPARATION OF THE SUBSTANCES

(75) Inventors: Masatoshi Tanouchi; Satoshi Tsuchiya, both of Nobeoka; Haruo Fukuhara, Narita; Hitoshi Nagasaki, Urawa, all of (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/529,969

(22) PCT Filed: Oct. 22, 1998

(86) PCT No.: PCT/JP98/04789

§ 371 Date: Apr. 24, 2000

§ 102(e) Date: Apr. 24, 2000

(87) PCT Pub. No.: WO99/21434

PCT Pub. Date: May 6, 1999

(30) Foreign Application Priority Data

Oct. 24, 1997 (JP) ............................................ 09-292633

(51) Int. Cl.$^7$ .......................... A61K 35/60; C12N 9/48; C12N 9/50
(52) U.S. Cl. ...................... 424/523; 424/547; 435/212; 435/219; 435/267; 435/268; 435/272
(58) Field of Search ................................. 435/212, 219; 424/523, 547

(56) References Cited

FOREIGN PATENT DOCUMENTS

| EP | B1535135 | 8/1995 |
|----|----------|--------|
| JP | A60130349 | 7/1985 |
| JP | A63105686 | 5/1988 |
| JP | A63164852 | 7/1988 |
| JP | A63185391 | 7/1988 |
| JP | A6450890 | 2/1989 |
| JP | A28298 | 1/1990 |
| JP | A235093 | 2/1990 |
| JP | A5123176 | 5/1993 |
| JP | A5236974 | 9/1993 |
| JP | A5507624 | 11/1993 |
| JP | 321970 | 11/1994 |
| JP | A977782 | 3/1997 |

OTHER PUBLICATIONS

English translation of JP 63–164852 (Jul. 1988).*
English translation of JP 60–130349 (Jul. 1985).*
Yagi et al., Journal of Fermentation and Bioengineering, vol. 69, No. 1, pp. 23–25 (1990).
Nomura et al., Reports of Kochi Prefectural Industrial Technology Center, No. 27, pp. 109–120 (1996).
Kusayama et al., Food and Development, vol. 22, No. 5, pp. 32–35 (1987).

* cited by examiner

*Primary Examiner*—Leon B. Lankford, Jr.
*Assistant Examiner*—Susan D. Coe
(74) *Attorney, Agent, or Firm*—Birch, Stewart, Kolasch & Birch, LLP

(57) ABSTRACT

A process for producing water-insoluble substances derived from fishes and shellfishes, includes the treating of the waste of fishes and shellfishes containing the substances with proteolytic enzymes under stirring to obtain an oil-in-water (O/W) type emulsified composition. This composition contains water-soluble amino-acids, oligoproteins having a molecular weight of not greater than 30,000, water-soluble minerals, water-insoluble highly unsaturated fatty acids and proteins (solid matter) having a molecular weight of 20,000 to 100,000, with 50% or more of all the proteins in said emulsified composition having a molecular weight of 20,000 to 100,000. Thereafter the emulsified composition is separated into solid and liquid phases, and the obtained solid composition containing proteins with a molecular weight of 20,000 to 100,000 and fats and oils is extracted with an organic solvent.

16 Claims, No Drawings

COMPOSITION CONTAINING USEFUL SUBSTANCES ORIGINATING IN FISHES AND SHELLFISHES AND PROCESS FOR THE PREPARATION OF THE SUBSTANCES

This application is the national phase under 35 U.S.C. § 371 of PCT International Application No. PCT/JP98/04789 which has an International filing date of Oct. 22, 1998, which designated the United States of America.

TECHNICAL FIELD

The present invention relates to a process for separating the water-insoluble (oil-soluble) useful substances economically from the wastes of fishes and shellfishes. More particularly, it relates to the said process featuring the steps of preparing a novel oil-in-water type emulsified composition from the wastes of fishes and shellfishes by treating the wastes with proteolytic enzymes to convert proteins in the wastes into oligoproteins having a molecular weight in a specified range, separating said composition into solid and liquid, and extracting the solid matter with an organic solvent.

BACKGROUND ART

It is needless to say that fishes and shellfishes are natural resources which are of vital importance as a nutrient for mankind. These fishes and shellfishes are processed in a variety of forms, and in the course of processing, their skins, guts, bones, etc., are discarded as industrial waste. Although part of such waste is utilized as fertilizer or stock feed, most of it, under the present situation, is left unrecycled and necessitates disposal at a great cost. The regulations on the method of disposal have become more rigorous recently, and the treatment of such waste is posing a serious problem from the aspect of environmental protection.

For instance, cuttlefish skin, which is discarded as industrial waste after hot-water processing, is estimated to produce at least 2,000 tons of waste per year in Japan. Recycling of such cuttlefish skin waste will be a great benefit to the prevention of environmental pollution in the sense of effective utilization of industrial waste. Also, by promoting recycling of waste matter which is presently disposed at a great expense, it will become possible to recover useful substances at a notably low cost.

It is known that these fish and shellfish wastes (skin, guts, bone, head, tail, fin, eyes of scallops, shell, and sometimes whole fish or shellfish body) contain various useful substances in large quantities or in low or only slight concentrations.

For instance, as water-soluble substances, various types of water-s,oluble vitamins, various types of minerals, polysaccharides, amino-acids, chondroitin sulfuric acid, enzymes, protamine, triglycerides of saturated or unsaturated lower fatty acids, etc., are known to exist in said wastes, and as water-insoluble substances, calcium, triglycerides of saturated higher fatty acids, triglycerides of unsaturated fatty acids (monoenoic acids such as myristoleic acid, palmitoleic acid and nervonic acid, tetraenoic acids such as arachidonic acid, pentaenoic acids such as clupanodonic acid, hexaenoic acids such as docosahexaenoic acid, etc.), phospholipids such as phosphaditidyl choline and phsphaditidyl ethanolamine, etc., are known to be contained in said waste.

These substances can be applied to a wide scope of uses, such as nutrition promoting foods, humectants, liquid crystal material, medicinal base material, antibacterial agents, preservatives, stock feed, etc., according to the particular properties of the substances.

Extraction from the natural products may be the best way for obtaining an desired compound with ease and at low cost if the selection of raw material is appropriate and an effective means for extraction is elaborated.

For example, an extensive search has been made for the materials containing docosahexaenoic acid (hereinafter abbreviated as DHA) in high concentrations, and the methods for preparing DHA from the head, guts or whole of the blue-back fishes such as tuna, bonito, saurel, macherel, sardine, etc., have been proposed (JP-A-63-164852 and JP-A-64-50890).

However, in view of the difficulty of the separating operations, attempts for yielding the objective useful substances are also being made using the artificial or natural materials other than fishes and shellfishes by introducing such techniques as synthetic reactions or enzymatic reactions for certain types of substances.

For instance, it has been reported that the glyceride esters of highly unsaturated fatty acids were synthesized by acyl group exchange between the fatty acids with a lipase (Journal of Fermentation and Bioengineering, Vol. 69, pp. 23–25, 1990).

Also, the techniques for obtaining a desired phospholipid derivative by enzymatic ester exchange or acylation from phospholipid or lysophospholipid and an optional fatty acid or fatty acid ester have been disclosed (JP-A-63-105686, JP-A-63-185391, JP-A-2-35093 and JP-A-5-236974). However, all of the above-mentioned reports or patents involve many problems, such as random entry of the introduced fatty acid into the sn-1 or sn-2 position and too low enzyme reaction rate, for realizing practical industrial application. Thus, a technique enabling extraction of a desired useful substance from selected waste containing such a substance in a higher concentration by a simple process has been desired.

A method featuring extraction of the desired substance from a microorganism cultured in a DHA-added medium has been also disclosed (JP-A-5-123176). Further, a method of preparing DHA from the guts of cuttlefish (JP-A-2-8298) and a method of preparing DHA from cuttlefish skin (JP-A-6-321970 and JP-A-9-77782), worked up in view of high DHA concentration in phospholipid of cuttlefish, have been reported.

In order to separate the useful substances from the fish body, generally the fish body is first divided into the water-soluble components and the water-insoluble components.

Usually steaming is employed for this treatment. When steam is passed through waste of fishes or shellfishes, oil is separated out. In this case, however, the interface between water and oil is ambiguous and it is hard to distinguish between the two phases, so that no perfect separation can be achieved and, in some cases, the whole sets to gel, making it impossible to carry out the separating operation.

Also, according to the above method, since steam heating is applied, the useful components which are unstable to heat may be denatured and loose their activity. Generally, the fish body components are prone to oxidize by the action of oxygen in the air to generate the so-called fish-smelling components (amines, aldehydes, etc.). Needless to say, the presence of such fish-smelling components greatly reduces the commercial value of the product. Lots of labor and cost (for high-degree vacuum distillation, etc.) are required for removing the fish smell. The similar problems are also raised in connection with the tinted matter with heating.

In order to remove water which accounts for about 90% of the overall fish body weight, it is practiced to dry the fish body by various methods such as lyophilization, spray drying, sun-drying, etc., and extract the useful substance from the dried product with a solvent (hexane, alcohol, etc.). This method, however, requires specific equipment such as a dryer, which leads to high production cost. And when heating is needed, there arises the problem of the denaturing of the useful components as mentioned above. Further, there may be situations where it is required to transport the material-to-be-processed with high water content to a treating plant which may not necessarily be located adjacent to the waste generating plant. Moreover, in case a refrigerator van or such is used for the transport, it is necessary to take sufficient measure to prevent putrefaction (if putrefaction begins, the commercial value of the material will be spoiled by the fish smell as mentioned above), and also the transportation cost will become a burden. Therefore, a drying treatment for removing water is usually conducted before extraction of the desired substance.

As means for removing water from a living specimen, various methods such as compression, air drying, heat drying, vacuum drying and freeze-drying are conceivable. For reducing water without changing the normal figure of the living specimen, compression alone is insufficient to attain a desired water removal rate while air drying, heat drying and vacuum drying involve the problem in respects of treating temperature and treating time. The operation cost of the freeze-dryer required for the said water removal is vast. In order to elevate the drying efficiency, the surface area of the specimen needs to be enlarged as much as possible. There is also required extra labor for feeding of the material to the freeze-dryer. Further, a freeze-dryer takes a long time to operate. The equipment investment for the freeze-dryer tends to be too heavy for elevating the production capacity. For these reasons, employment of the freeze-drying step in an industrial process is disadvantageous. Thus, a simple and inexpensive dehydration method that can replace the conventional freeze-drying treatment without affecting the product quality has been desired.

Certain types of waste of fishes and shellfishes, for instance cuttlefish skin, are covered on their surface with a slimy substance composed of a polysaccharide. This substance is often responsible for a large reduction of the filtering rate in the filtration step that is conducted in the process of phospholipid extraction with a solvent.

The present invention provides the techniques for easily and economically extracting the water-soluble and water-insoluble useful substances from the waste of fishes and shellfishes under the mild operating conditions that will not cause denaturing of these useful substances.

We have made studies in search of the solution to the various problems mentioned above. We have treated waste of fishes and shellfishes by using various types of proteolytic enzymes to degrade proteins, centrifuged them to separate the paste and the extract according to the degree of proteolysis, and investigated the condition of separation of oils and fats.

As a result, it was found that when an emulsified material obtained after treating waste with a certain combination of proteolytic enzymes was centrifuged, the material could be definitely separated into the phase of aqueous solution substantially free of oils and the sediment portion containing oils.

More specifically, when waste of fishes or shellfishes was treated by using specific proteolytic enzymes to degrade proteins in the waste to make a mixture of the water-soluble low-molecular weight peptides and amino-acids and the water-insoluble high-molecular weight peptides, the mixture was formed in a state of emulsion that has never been reported before. When this novel emulsified material was centrifuged by an ordinary method, it was easily separated into the sediment containing oils and the aqueous layer substantially free of oils. In the sediment obtained in the manner described above, there were contained water-insoluble proteins and fats, and about 90% of the whole fats and oils was recovered as sediment. It was confirmed that the collected fats and oils contained triglycerides and phosphaditydiyl choline of the higher unsaturated fatty acids such as eicosapentanic acid and docosahexaenoic acid. The above finding underlies the present invention.

DISCLOSURE OF THE INVENTION

The present invention is directed to the following embodiments:

(1) A process for producing water-insoluble useful substances derived from fishes and shellfishes, which comprises the steps of:
  (a) treating waste of fishes and shelifishes containing useful substances with a proteolytic enzyme(s) under stirring to obtain an oil-in-water (O/W) type emulsified composition comprising (i) water-soluble components which comprise water-soluble amino-acids, oligoproteins having a molecular weight of not greater than 30,000, vitamins and water-soluble minerals such as salts, and (ii) water-insoluble components, as solid matter, comprising oils and fats containing water-insoluble highly unsaturated fatty acids and proteins having a molecular weight of 20,000 to 100,000; wherein 50% or more of all the proteins in the emulsified composition have a molecular weight of 20,000 to 100,000;
  (b) separating said emulsified composition into solid and liquid phases to obtain a solid composition; and
  (c) extracting said solid composition with an organic solvent.

(2) An oil-in-water (O/W) type emulsified composition obtained by treating waste of fishes and shellfishes containing useful substances with a proteolytic enzyme(s) under stirring, which comprises (i) water-soluble components comprising water-soluble amino acids, oligoproteins having a molecular weight of not greater than 30,000, vitamins and water-soluble minerals such as salts, and (ii) water-insoluble components, as solid matter, comprising oils and fats containing water-soluble highly unsaturated fatty acids and proteins having a molecular weight of 20,000 to 100,000, wherein 50% or more of all the proteins in the emulsified composition have a molecular weight of 20,000 to 100,000.

(3) A novel solid composition comprising proteins having a molecular weight of 20,000 to 100,000 and oil and fat matter, obtained by separating the emulsified composition set out in (2) above into solid and liquid phases.

(4) A process as described in (1) above, wherein at least two enzymes selected from 1) an endo-type proteolytic enzyme, 2) an exo-type proteolytic enzyme and 3) an endo- and exo-type proteolytic enzyme are used in combination as said proteolytic enzymes.

(5) A process as described in (1) above, wherein the molecular weight of the proteins after the treatment is 30,000 to 50,000.

(6) A solid composition as set out in (3) above, wherein 50% or more of the whole protein after the treatment has a molecular weight of 30,000 to 50,000.

(7) A process as described in (1) above, wherein the waste is cuttlefish skin.

(8) A process as substantially described in (1) above, wherein the waste is eyeballs or spawn of salmon or tuna.

(9) A process as described in (1) above, wherein the useful substance is a phospholipid type highly unsaturated fatty acid.

(10) A process as described in (1) above, wherein the useful substance is phospholipid type DHA.

(11) A process as described in (1) above, wherein the solid matter after separation into solid and liquid phases is dried and then extracted with an organic solvent.

(12) A process as described in (1) above, wherein the organic solvent is selected from the group consisting of ethanol, hexane, acetone and a mixture thereof.

(13) A water-insoluble useful substance derived from fishes and shellfishes, obtained by extracting the solid composition described in (3) above with an organic solvent.

(14) An edible composition containing 35% or more of a phospholipid(s), a highly unsaturated fatty acid(s) in an amount of 40% or more based on the whole fatty acids in the phospholipid(s), and proteolytic enzyme-treated matter of fishes and shellfishes.

BEST MODE FOR CARRYING OUT THE INVENTION

In the present invention, as the first step, waste of fishes or shellfishes containing the objective useful substances is treated with a proteolytic enzyme(s) under stirring. In this case, it will be expedient to crush the waste depending on its form, state of existence, etc., as such crushing increases the surface area of the waste matter to be treated to allow more smooth proceeding of the enzyme reaction. Powdery waste may not require such pre-treatment. In the present invention, crushing and stirring can be well effected by the commonly used means, and no specific devices are required therefor.

Generally, this type of waste can be easily crushed as it is usually kept frozen in order to prevent putrefaction. Crushing and stirring are performed for the purpose of promoting smooth progress of the enzyme reaction, and to this end it suffices to crush the material (waste) to a grain size of about 0.01 to 0.1 cm. For instance, a commercial food processor available from Nakabe Corporation can be conveniently used for this purpose. Some types of waste contain bone tissues such as broken pieces of bone and shells, but since they settle down as a sediment together with oils and fats, they won't disturb the process of the present invention. In the case of the waste with a low water content, such as the eyeballs of tuna, it is advisable to add water for elevating fluidity so as to increase the efficiency of contact with enzymes. The water added is separated from the sediment, so that it will not obstruct extraction of the useful oil and fat material, allowing the fulfillment of the object of the invention.

As the stirring means, it is possible to use an ordinary stirrer provided with one or two turbine or propeller type stirring vanes. The stirrer capacity, although variable depending on the shape of the blade, the size of the reactor used and the nature of the liquid to be treated, is preferably around 20 to 100 rpm when using a reactor with a volume of about 1 m$^3$. Technologically, the power required per unit volume of the material to be stirred is referred to as a practical measure of stirring efficiency. For the reaction in the present invention, such stirring efficiency preferably falls in the range of about 0.5 to 5 KW/m$^3$. Stirring too slowly may cause accumulation of the crushed waste sediment in the reactor which retards the progress of the reaction. Stirring too strongly may cause the formation of a creamy emulsion which greatly hinders solid-liquid separation in the next step.

The proteolytic enzymes which can be used in the present invention include endo-type peptidases (enzymes of the type which breaks the protein linkage at its middle point), exo-type peptidases (enzymes of the type which breaks the protein linkage at an end; the enzyme which breaks the linkage at its N end is called aminopeptidase, and the enzyme which breaks the linkage at its C end is called carboxypeptidase), and endo- and exo-type peptidases having the functions of both endo-type and exo-type enzymes. In the present invention, it is more effective to use a mixture of two or more types of said enzymes than to use only one type.

The concentration of the proteolytic enzymes used in the present invention is 0.1 to 10% by weight, preferably 0.5 to 2% by weight based on the overall amount of protein. The enzyme reaction conditions should be selected with care according to the type of the waste to be treated for obtaining a desired form of emulsion. It is to be noted that if the proteolytic reaction of protein proceeds to excess to reduce the protein molecular weight to less than 20,000, the aqueous phase/oil phase separation becomes difficult to attain, making it impossible to obtain an emulsified composition having the effect of the present invention. Also, if the post-reaction residual protein becomes small in quantity as compared to the oils and fats, the latter may not be sufficiently taken up in the solid, or oil may ooze out during drying of the obtained solid sediment, giving rise to problems, such as cumbersome handling of the material. Of course, it is impossible to obtain the effect of the present invention when degradation has advanced perfectly to the formation of an amino acid or an oligo-protein akin thereto.

Conversely, if proteolysis is insufficient and the molecular weight of protein stays above 100,000, it is also impossible to derive the effect of the present invention.

Gel filtration, SDS electrophoresis and other methods are known for the determination of molecular weight. Gel filtration is simple and practical, but one needs to pay attention to the interaction with the carrier. When using electrophoresis, the molecular weight can be determined by using a mixture of phospholipase b (MW 94,000), albumin (MW 67,000), ovalbumin (MW 43,000), carbonic anhydrase (MW 30,000), trypsin inhibitor (MW 20,000) and α-lactalbumin (14,000) as an MW marker. It is also possible to determine the amount of protein, along with its molecular weight, from the degree of color development of protein in the electrophoresis. The average molecular weight of protein in fishes and shellfishes is usually around 600,000, but in order to obtain the effect of the present invention, it is imperative to make a composition in which 50% or more, preferably 70% or more of the whole protein has a molecular weight in the range of 20,000 to 100,000, more preferably 30,000 to 50,000, by the techniques of the present invention.

Oligopeptides having a molecular weight falling in the above-defined range have an emulsion-forming effect, that is, its water-soluble component and the oil-adsorbed solid protein cooperate to form an emulsified state. The present inventors found that in this operation, quite surprisingly, oil is scarcely distributed to the aqueous layer and forms a mixture with the solid protein. Consequently, the aqueous layer and the oil layer can be separated distinctly from each other by a simple solid/liquid separating method. Since oil settles down with sedimentation of solid protein, it can be easily separated from the aqueous layer.

Solid/liquid separation can be effected by using a spontaneously settling thickener or a filter, but it is preferred to use a centrifuge which allows faster treatment. The basket type and decanter type centrifuges can be used. Industrially the decanter type is preferred as it is capable of continuous treatment.

The enzyme reaction conditions for degrading protein into the above-defined range of molecular weight needs to be set in consideration of the optimal temperature or heat resistance of the enzymes used and the type of the waste to be treated as mentioned before, but usually the reaction temperature is 30 to 80° C. and the reaction time is 0.5 to 5 hours, preferably the reaction temperature is 30 to 50° C. and the reaction time is 1 to 2 hours. An antioxidant such as vitamin C, tocopherol, vitamin E cr catechin may be added to the reaction system to suppress oxidation during the reaction. In order to prevent the enzyme reaction from advancing more than necessary, the enzymes are preferably deactivated after the desired emulsified state has been obtained. This can be usually effected by heating at 80 to 100° C. for 5 to 20 minutes.

In the thus obtained emulsion, the water-insoluble proteins are degraded by the enzymes while the water-soluble amino-acids and low-molecular weight peptides are increased. Also, the saccharides in the cells and the salts which have been combined with proteins are made soluble in water. The normally water-soluble components are transferred to the aqueous layer while the water-insoluble ones are shifted to the sediment layer. Said water-insoluble oils and fats have substantially been recovered in the sediment.

The water content in waste of fishes and shellfishes is usually 80 to 90%, but the sediment obtained in the manner described above is about 2 to 10% of the pre-treatment waste in weight, and the water content of such a sediment is about 40 to 70%, usually around 65%. Thus, the water content per unit amount of the useful substances is greatly reduced in comparison with the pre-treatment waste, which signifies a remarkable reduction of cost and labor required for drying removal of water in separation and extraction of oils and proteins.

The wet sediment is preferably dried to a water content of 10% or less, preferably 2% or less, because of elevated extraction efficiency. In this case, too, the cost for drying is drastically lessened as the useful substances are concentrated in the sediment and reduced in quantity.

Because of the enzyme reaction, no severe heating such as that conducted in steaming is necessary, and the desired concentration can be effected without causing denaturing of the useful substances which are unstable to heat.

The sediment is extracted with an organic solvent (chloroform, dichloromethane, methanol, ethanol, acetone, hexane, toluene, etc.). If necessary, it may be dried before extraction. An effective solvent or composite solvent is selected in consideration of the type of the waste to be treated, the type and amount of the objective useful substance(s) and other factors. For instance, ethanol, hexane and the like are effective for extracting DHA phospholipids. In the extract obtained by the process of the present invention, phospholipids are contained at a high rate of over 35%, and the higher unsaturated fatty acids such as docohexaenoic acid and eicosapentaenoic acid are also contained at a rate of over 40% of the whole fatty acids. It is also a merit to this invention that high-purity phospholipids can be extracted even from the waste material which may not necessarily be high in phospholipid concentration. Further, the lipids obtained according to the present invention contain small quantities of oligoproteins produced by the proteolytic enzymes and various kinds of phospholipids, so that the composition of the present invention is expected to possess excellent physiological activity when used in foods. It is known that some of the substances obtained from enzymatic treatment of fish proteins have a gentle blood pressure reducing action. Such physiologically active substances often exhibit a physiologically more desirable effect when mixed with other materials than when they are present singly with high purity. Such an effect is often seen in various kinds of herbs. Therefore, when using the useful substances of the present invention as a component of health foods, a more desirable effect may be expected from a purity of such a standard as obtained by extraction. The extracted active substances may be further purified by the conventional methods such as recrystallization, chromatography, filtration, etc., which are properly selected according to the situation, to obtain a high-purity physiologically active substance which can be offered, for instance, to medicinal and pharmaceutical uses. The phospholipids mentioned above can also be enhanced in purity by crystallizing their hexane extract with acetone which is a poor solvent of phospholipids.

The sediment is dried and then, if necessary, ground to give a powder rich with useful substances such as DHA. Therefore, the powder can be used either as a material from which to extract the useful substances with higher purity or may be used as it is as functional foods or feed for aquarium fishes, cattle, pets, etc. Since the product contains the useful substance(s) and is of powdery form, it is easy to handle and unsusceptible to air oxidation and other forms of denaturalization. The separated aqueous phase portion also contains many useful substances, so that it can be used in the form as it is (extract from fishes and shellfishes) as foods or feed for aquarium fishes, pets, etc. This extract can also be used as a material from which to further extract the useful substance (s) by suitable means such as solvent extraction or chromatography to obtain a high purity product. As described above, the present invention provides the techniques for economically separating the water-soluble or water-insoluble useful substances contained in the wastes of fishes and shellfishes.

The present invention will be further illustrated by the following examples and comparative examples, but the invention is not subject to any restrictions by these examples.

EXAMPLE 1

The frozen cuttlefish skin was crushed by a food processor (mfd. by Nakabe Corp.) and 1,000 g thereof was weighed into a 2,000 ml beaker. The beaker was fixed in a water bath, and a variable-speed stirrer (mfd. by EYELA Inc.) provided with a stirring rod was set in the center of the beaker.

The crushed mass of cuttlefish skin was heated to 50C with stirring at 500 rpm. When the mass being stirred reached 50° C., there were added thereto 0.3% of endo-type Alkalase (produced by Novo Industry Ltd.), 0.3% of exo-type Amano M (produced by Amano Pharmaceutical Co., Ltd.), 0.3% of exo- and endo-type Amano A (produced by Amano Pharmaceutical Co., Ltd.) and 0.1% of deaminase (produced by Daiwa Chemical Co., Ltd.) for improving the taste and smell of the water-soluble substance expected to be yielded, viz. the extract, each of said additives being dissolved in a small quantity of water (% being based on the material to be treated).

Vitamin E was also added in an amount of 0.3% based on the oils and fats contained in the mass. Then the mass was subjected to an enzyme reaction for 2 hours maintaining the temperature at 50° C., followed by additional 15-minute treatment at 90° C. to deactivate the enzymes.

After the enzyme reaction, the resulting solution (O/W type emulsified composition) was diluted and subjected to electrophoretic assay, which showed approximately 75% of the original proteins had been made to possess a molecular weight of 31,000 by the above treatment.

The thus obtained emulsified composition was cooled, put into a tube of a high-speed centrifuge (mfd. by Hitachi Ltd.) and centrifuged at 10,000 rpm for 20 minutes to separate the composition into solids and water-soluble matter.

On conclusion of centrifuging, the centrifuge tube was taken out, the water-soluble matter was transferred to a beaker, and 120 g of the sediment was scraped out, transferred to a stainless steel-made plate vat and, with the sediment deposited to a thickness of 3 to 5 mm on the vat, placed in a 50 to 60° C. dryer (mfd. by Tabai Co., Ltd.) where it was dried for 12 hours. The dried product was removed from the vat and applied to a small-sized grinder (mfd. by Iwatani Co., Ltd.) to give 31 g of powder.

As a result of the above operations, the following data were obtained from the separated solids and water-soluble matter. Water content was determined by the Karl-Fischer method and oil content was determined by the conventional gravimetric method involving chloroform extraction. The data obtained from similar determinations of raw cuttlefish skin and dried powder thereof are also shown.

|  | Water | Oil |
|---|---|---|
| Raw cuttlefish skin | 92.2% | 1.5% |
| Dry powder of cuttlefish skin | 1.2 | 19.8 |
| Dry powder of solid composition of the present invention | 0.8 | 32.9 |
| Water-soluble matter | 93.5 | 0.2 or less |

As is seen from the above table, the oil and fat content in the dry powder of the solid composition of the present invention is higher by 21.9 times and 1.7 times, respectively, than those in the raw cuttlefish skin and in the powder obtained by simply directly drying the cuttlefish skin. It will be also seen that oils and fats are scantly in the water-soluble matter. A quantitative analysis of oil in the dry powder by YEATROSCAN confirmed the presence of 12.7% of phosphaditidyl choline and 8.3% of phosphaditidyl ethanolamine. Gas chromatographic determination of fatty acids after hydrolytic ester exchange showed the presence of 38.1% of docosahexaenoic acid and 10% of eicosapentaenoic acid. This corroborates that docosahexaenoic acid of phosphaditidyl choline and eicosapentaenoic acid derivatives had been extracted in high concentrations in the solid composition centrifuged according to the method. of the present invention.

In a similar analysis of 9 g of a cake obtained by subjecting the dry powder of said solid composition to ethanol extraction and, after drying, hexane extraction, followed by crystallization and sedimentation with acetone which is a poor solvent of phosphaditidyl choline, and finally filtration by Nutsche funnel, it was confirmed that the cake contained 38.5% of phosphaditidyl choline and 11.4% of phosphaditidyl ethanolamine. Further, the result of a fatty acid analysis showed the presence of 39.5% of docosahexaenoic acid and 13% of eicosapentaenoic acid. It was thus possible to obtain high-purity phosphaditidyl choline and phosphaditidyl ethanolamine.

Comparative Example 1

The same procedure as in Example 1 was carried out except that the reaction time was prolonged to 4 hours. As a result, the amount of the solids obtained after centrifuging was as very small as 5 g. Also, the oil content in the obtained solids was 8%, and it was impossible to recover a sufficient amount of oil. Electrophoretic analysis of the enzyme reaction solution showed 87% of the original proteins had a molecular weight of not greater than 15,000.

Comparative Example 2

The same procedure as in Example 1 was carried out except that the reaction time was shortened to one hour. The best part of the enzyme reaction product gelled, and it was impossible to perform centrifugation. The liquid phase fraction was centrifuged to obtain 12 g of sediment, but the oil and fat content in the sediment was only 8.5% and it was impossible to recover a sufficient amount of oil. Electrophoretic analysis of the enzyme reaction solution showed that 46% of the original proteins had a molecular weight of approximately 120,000 and 31% had a molecular weight of not less than 130,000.

EXAMPLE 2

Frozen krills were crushed by a food processor (mfd. by Nakabe Corp.) and 1,000 g thereof was weighed into a 2,000 ml beaker. The beaker was fixed in a water bath and a variable-speed stirrer (EYELA Inc.) provided with a stirring rod was set in the center of the beaker.

The crushed mass of krills was heated to 50° C. with stirring at 500 rpm. When the mass being stirred reached 500° C., there were added thereto 0.5% of an endo-type protease YP-SS (produced by Yakult Chemical Co., Ltd.) and 0.5% of an exo-type Alloase P-10 (produced by Yakult Chemical Co., Ltd.), each being dissolved in a small quantity of water (% being based on the material to be treated). Vitamin E was also added in an amount of 0.3% based on the oils and fats contained in the material. Then the mass was allowed to undergo enzyme reaction for one hour while maintaining the temperature at 50° C., followed by additional 15-minute treatment at 90° C. to deactivate the enzymes. After the reaction, the resulting solution (O/W type emulsified composition) was diluted and subjected to electrophoretic analysis, which showed approximately 65% of the original proteins came to have a molecular weight of 37,000.

The thus obtained emulsified composition was cooled, then put into a tube of a high-speed centrifuge (mfd. by Hitachi Ltd.) and centrifuged at 10,000 rpm for 20 minutes.

After centrifuging, the centrifuge tube was taken out, the water-soluble fraction in the upper part of the tube was transferred to a beaker, and the solid composition was scraped out and transferred to a stainless steel-made plate vat. To 92 g of the obtained sediment, water was added in an amount of 25% based on the solid composition to form an aqueous solution, and the latter was dried by a laboratory spray dryer (mfd. by Freund Inc.) to give 33 g of dry powder.

As a result of the above operations, the following data were obtained from the separated solids and water-soluble fraction.

Water content was determined by the Karl-Fischer method and oil and fat content was determined by the conventional gravimetric method involving chloroform extraction. The data obtained from similar determinations of raw krills and dry powder thereof are also shown.

|  | Water | Oil |
| --- | --- | --- |
| Raw krills | 78.5% | 3.1% |
| Dry powder of krills | 1.0 | 13.9 |
| Dry powder of the solid composition of the present invention | 1.2 | 48.5 |
| Water-soluble fraction | 94.2 | 0.2 or less |

As is seen from the above table, the oil and fat content in the dry powder of the solid composition of the present invention is higher by 15.6 times and 3.5 times, respectively, than those in the raw krills and in the powder obtained by simply directly drying the krills. It will be also seen that oils and fats are scantly in the water-soluble fraction.

EXAMPLE 3

The frozen tuna eyeballs were crushed by a food processor (mfd. by Nakabe Corp.), and 1,000 g thereof was weighed into a 3,000 ml beaker together with 1,000 g of water. The beaker was fixed in a water bath, and a variable-speed stirrer (mfd. by EYELA Inc.) provided with a stirring rod was set in the center of the beaker.

The crushed mass of tuna eyeballs was heated to 50° C. with stirring at 500 rpm. When the mass being stirred reached 50° C., there were added thereto 0.5% of an endo-type protease YP-SS (produced by Yakult Chemical Co., Ltd.) and 0.5% of an exo-type Alloase P-10 (produced by Yakult Chemical Co., Ltd.), each being dissolved in a small quantity of water (% being based on the material to be treated). Vitamin E was also added in an amount of 0.3% based on the oils and fats contained in the material. Then the mass was allowed to undergo an enzyme reaction for one hour while maintaining the temperature at 50° C., followed by additional 15-minute treatment at 90° C. to deactivate the enzymes. The resulting reaction solution (O/W type emulsified composition) was diluted and then subjected to electrophoretic analysis, which showed approximately 82.5% of the original proteins had a molecular weight of 41,000 after the treatment.

The thus obtained emulsified composition was cooled, put into a tube of a high-speed centrifuge (mfd. by Hitachi Ltd.) and centrifuged at 10,000 rpm for 20 minutes.

On completion of centrifuging, the centrifuge tube was taken out, the water-soluble fraction in the upper part of the tube was transferred to a beaker, and the solid composition was scraped out and transferred to a stainless steel plate vat. To 620 g of the obtained solid composition, water was added in an amount of 25% based on the solid composition to form an aqueous solution, and the latter was dried by a laboratory spray dryer (mfd. by Freund Inc.) to give 226 g of dry powder. As a result of the above operations, the following data were obtained from the separated solids and water-soluble fraction.

Water content was determined by the Karl-Fischer method and oil and fat content was determined by the conventional gravimetric method involving chloroform extraction. The data obtained from similar determinations of the raw tuna eyes and dry powder thereof are also shown.

|  | Water | Oil |
| --- | --- | --- |
| Raw tuna eyeballs | 66.5% | 21.1% |
| Dry powder of tuna eyeballs | 1.6 | 34.6 |
| Dry powder of solid composition of the present invention | 1.2 | 55.7 |
| Water-soluble fraction (concentrated) | 91.5 | 1.2 |

As is seen from the above table, the oil and fat content in the dry powder of the sediment according to the present invention is higher by 2.6 times and 1.6 times, respectively, than those in the raw tuna eyeballs and the powder obtained by directly drying the tune eyeballs. It will be also seen that oils and fats are scantly in the water-soluble fraction.

EXAMPLE 4

The frozen guts of sardine were crushed by a food processor (mfd. by Nakabe Corp.) and 1,000 g thereof was weighed into a 3000 ml beaker, to which 1,000 g of water was further added. The beaker was fixed in a water bath and a variable-speed stirrer (mfd. by EYELA Ltd.) provided with a stirring rod was set in the center of the beaker.

The crushed mass of sardine guts was heated to 50° C. with stirring at 500 rpm. When the mass reached 50° C., there were added thereto 0.3% of endo-type Alkalase (produced by Novo Industry Ltd.), 0.3% of exo-type Amano M (produced by Amano Pharmaceutical Co., Ltd.), 0.3% of exo- and endo-type Amano A (produced by Amano Pharmaceutical Co., Ltd.) and 0.1% of deaminase (produced by Daiwa Chemical Co., Ltd.) for improving the taste and smell of the water-soluble fraction expected to be yielded, i.e. the extract, each being dissolved in a small quantity of water (% being based on the material to be treated). Vitamin E was also added in an amount of 0.3% based on the oils and fats contained in the material. Then the mass was allowed to undergo an enzyme reaction for 2 hours while maintaining the temperature at 50° C., followed by 15-minute enzyme deactivating treatment at 90° C. The resulting solution (O/W type emulsified composition) was diluted and subjected to electrophoretic analysis, which showed approximately 67% of the original proteins had a molecular weight of 31,000 after the treatment.

The thus obtained emulsified composition was cooled, then put into a tube of a high-speed centrifuge (mfd. by Hitachi Ltd.) and centrifuged at 10,000 rpm for 20 minutes.

After centrifuging, the centrifuge tube was taken out and 1,570 g of the water-soluble fraction in the upper part of the tube was transferred to a beaker while the solid composition was scraped out and trans-ferred to a stainless steel plate vat. To 520 g of the obtained solid composition, water was added in an amount of 25% based on the composition to form an aqueous solution, and the latter was dried by a laboratory spray dryer (mfd. by Freund Inc.) to give 250 g of dry powder. As a result of the above operations, the following data were obtained from the separated solids and water-soluble fraction.

Water content was determined by the Karl-Fischer method while the oil and fat content was determined by the conventional gravimetrical method involving chloroform extraction. The data obtained from similar determinations of the raw sardine guts and dry powder of sardine guts are also shown.

|  | Water | Oil |
| --- | --- | --- |
| Raw sardine guts | 67.4% | 18.9% |
| Dry powder of sardine guts | 1.3 | 45.2 |
| Dry powder of solid composition of the present invention | 1.5 | 74.1 |
| Water-soluble fraction | 93.1 | 1.8 |

As is seen from the above table, the oil and fat content in the dry powder of the solid composition according to the present invention is higher by 3.9 times and 1.6 times, respectively, than those in the raw sardine guts and the powder obtained by simply directly drying the sardine guts. It will be also seen that oils and fats are scantly in the water-soluble fraction.

INDUSTRIAL APPLICABILITY

The present invention provides a process for obtaining the water-soluble and water-insoluble useful substances from the waste of fishes and shellfishes by forming a novel oil-in-water (O/W) type emulsified composition containing oils and fats and solid proteins from the waste, and separating this emulsified composition into solid and liquid to obtain a novel solid composition. Use of the solid composition of the present invention as the starting material enables economical and industrial extraction of the useful substances contained in the waste of fishes and shellfishes which, in the past, has required troublesome steps and has not necessarily been high in yield. Also, the present invention helps to pave the way for economical utilization of the waste and produces a large effect in reducing environmental pollution by waste disposal which has become more and more serious in recent years.

What is claimed is:

1. A process for producing water-insoluble substances derived from fishes and shellfishes, which comprises the steps of:
   (a) treating portions of fishes and shellfishes containing said substances with a proteolytic enzyme under stirring to obtain an oil-in-water (O/W) type emulsified composition comprising, (i) water-soluble components which comprise water-soluble amino-acids, oligoproteins having a molecular weight of not greater than 30,000, vitamins and water-soluble minerals, and (ii) water-insoluble components, as solid matter, comprising oils and fats containing water-insoluble unsaturated fatty acids and proteins having a molecular weight of 20,000 to 100,000, wherein at least 50% of all the proteins in said emulsified composition have a molecular weight of 20,000 to 100,000;
   (b) separating said emulsified composition into solid and liquid phases to obtain a solid composition; and
   (c) extracting said solid composition with an organic solvent.

2. An oil-in-water (O/W) type emulsified composition obtained by treating portions of fishes and shellfishes containing said composition of substances with a proteolytic enzyme under stirring, which comprises (i) water-soluble components comprising water-soluble amino-acids, oligoproteins having a molecular weight of not greater than 30,000, vitamins and water-soluble minerals, and (ii) water-insoluble components, as solid matter, comprising oils and fats containing water-insoluble highly unsaturated fatty acids and proteins having a molecular weight of 20,000 to 100,000, wherein at least 50% of all the proteins in the emulsified composition have a molecular weight of 20,000 to 100,000.

3. A solid composition comprising proteins having a molecular weight of 20,000 to 100,000 and oils and fats, obtained by separating into solid and liquid phases an oil-in-water (O/W) type emulsified composition, which is obtained by treating portions of fishes and shellfishes containing said composition with a proteolytic enzyme under stirring; wherein the oil-in-water (O/W) type emulsified composition comprises water-soluble amino acids, oligoproteins having a molecular weight of not greater than 30,000, water-soluble minerals, oils and fats containing water-insoluble highly unsaturated fatty acids and proteins having a molecular weight of 20,000 to 100,000 wherein at least 50% of all the proteins in the emulsified composition have a molecular weight of 20,000 to 100,000.

4. A process according to claim 1, wherein at least two enzymes selected from the group consisting of (1) an endo-type proteolytic enzyme, (2) an exo-type proteolytic enzyme and (3) an endo- and exo-type proteolytic enzyme are used in combination as the proteolytic enzymes.

5. A process according to claim 1, wherein the molecular weight of the proteins after treatment is 5 30,000 to 50,000.

6. A solid composition according to claim 3, wherein 50% or more of the proteins after treatment have a molecular weight of 30,000 to 50,000.

7. A process according to claim 1, wherein the portions comprise cuttlefish skin.

8. A process according to claim 1, wherein the portions comprise eyeballs or spawn of salmon or tuna.

9. A process according to claim 1, wherein the substance is a phospholipid type unsaturated fatty acid.

10. A process according to claim 1, wherein the substance is phospholipid type DHA.

11. A process according to claim 1, wherein the solid matter after separation from the liquid phase is dried and then extracted with an organic solvent.

12. A process according to claim 1, wherein the organic solvent is selected from the group consisting of ethanol, hexane, acetone and a mixture thereof.

13. Water-insoluble substances derived from fishes and shellfishes, obtained by extracting the solid composition set forth in claim 3 with an organic solvent.

14. An edible composition containing at least 35% based on a dry cake of the edible composition of a phospholipid, an unsaturated fatty acid in an amount of at least 40% based on the whole fatty acids in the phospholipid, and proteolytic enzyme-treated matter of fishes and shellfishes.

15. A solid composition according to claim 2, wherein 50% or more of all the proteins in the emulsified composition have a molecular weight of 30,000 to 100,000.

16. A solid composition according to claim 3, wherein 50% or more of all the proteins in the emulsified composition have a molecular weight of 30,000 to 100,000.

* * * * *